(12) United States Patent
Stottlemyre et al.

(10) Patent No.: US 10,226,495 B2
(45) Date of Patent: Mar. 12, 2019

(54) HAIR LOSS COMPOSITIONS AND METHODS OF MAKING AND USING SAME

(71) Applicant: The Beauty Cartel, LLC, Kingston, OK (US)

(72) Inventors: Denny Esco Stottlemyre, Mannsville, OK (US); Ronald Dale Reynolds, Kingston, OK (US)

(73) Assignee: The Beauty Cartel, LLC., Kingston, OK (US)

( * ) Notice: Subject to any disclaimer, the term of this patent is extended or adjusted under 35 U.S.C. 154(b) by 534 days.

(21) Appl. No.: 14/763,747

(22) PCT Filed: Jan. 29, 2014

(86) PCT No.: PCT/US2014/013631
§ 371 (c)(1),
(2) Date: Jul. 27, 2015

(87) PCT Pub. No.: WO2014/120793
PCT Pub. Date: Aug. 7, 2014

(65) Prior Publication Data
US 2015/0359830 A1  Dec. 17, 2015

Related U.S. Application Data

(60) Provisional application No. 61/758,618, filed on Jan. 30, 2013.

(51) Int. Cl.
| | | |
|---|---|---|
| A61K 36/48 | (2006.01) |
| A61K 36/00 | (2006.01) |
| A61K 36/14 | (2006.01) |
| A61K 8/64 | (2006.01) |
| A61Q 7/00 | (2006.01) |
| A61K 8/97 | (2017.01) |
| A61K 38/07 | (2006.01) |
| A61K 8/92 | (2006.01) |
| A61K 31/352 | (2006.01) |
| A61K 38/03 | (2006.01) |

(52) U.S. Cl.
CPC .............. *A61K 36/14* (2013.01); *A61K 8/64* (2013.01); *A61K 8/922* (2013.01); *A61K 8/97* (2013.01); *A61K 31/352* (2013.01); *A61K 36/48* (2013.01); *A61K 38/03* (2013.01); *A61K 38/07* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 6,184,247 B1 | 2/2001 | Schneider | |
| 6,579,516 B1 | 6/2003 | Mansouri | |
| 7,081,258 B2 * | 7/2006 | Hwang | A61K 8/35 424/725 |
| 7,507,719 B2 | 3/2009 | Pinel et al. | |
| 8,197,865 B2 * | 6/2012 | Glynn | A61K 8/678 424/725 |
| 8,227,426 B2 * | 7/2012 | Gupta | A61K 8/347 424/70.13 |
| 2004/0213859 A1 | 10/2004 | Zelickson | |
| 2008/0317795 A1 * | 12/2008 | Traynor | A61K 8/062 424/401 |
| 2012/0052032 A1 * | 3/2012 | Yamaki | A61K 8/342 424/70.1 |
| 2014/0135372 A1 * | 5/2014 | Farber | A61K 9/06 514/390 |

FOREIGN PATENT DOCUMENTS

| | | | |
|---|---|---|---|
| CN | 101697949 A | * | 4/2010 |
| WO | WO2005002608 A | * | 1/2005 |
| WO | 2014120793 A1 | | 8/2014 |

OTHER PUBLICATIONS

Evans, B. A. J., et al., "Inhibition of 5α-reductase in genital skin fibroblasts and prostate tissue by dietary lignans and isoflavonoids," Journal of Endocrinology, 1995, pp. 295-302, vol. 147.
Filing receipt and specification for provisional patent application entitled "Hair Loss Treatment Compositions and Methods of Making and Using Same," by Denny Esco Stottlemyre, et al., filed Jan. 30, 2013 as U.S. Appl. No. 61/758,618.
Foreign communication from a related counterpart application—International Search Report and Written Opinion, PCT/US2014/013631, dated May 20, 2014, 12 pages.
Foreign communication from a related counterpart application—International Preliminary Report on Patentability, PCT/US2014/013631, dated Aug. 4, 2015, 9 pages.
Lee, Geun-Shik, et al., "The essential oils of Chamaecyparis obtusa promote hair growth through the induction of vascular endothelial growth factor gene," Fitoterapia, 2010, pp. 17-24, vol. 81, Elsevier B.V.
Loing, Estelle, et al., "A new strategy to modulate alopecia using a combination of two specific and unique ingredients," Journal of Cosmetic Science, Jan./Feb. 2013, pp. 45-58, vol. 64.
Lucas Meyer Cosmetics technical file entitled "Capixyl™," www.lucasmeyercosmetics.com, pp. 1-45.
Park, Young-Ok, et al. "The Effects of Chamaecyparis Obtusa Oil on the Activities of Enzyme Relevant to Hair Growth," J. Kor. Soc. Cosm., 2008, pp. 355-364, vol. 14, No. 2.
South African Pharmaceutical & Cosmetic Review, "Hair loss solution," http://www.pharmacos.co.za/personal-care/37-hair-care/903-capixyl-the-new-hair-loss-solution, Jun. 25, 2012, 2 pages.

* cited by examiner

*Primary Examiner* — Christopher R Tate
*Assistant Examiner* — Randall Winston
(74) *Attorney, Agent, or Firm* — Andrew M. Metraller; Conley Rose, P.C.

(57) ABSTRACT

A composition for promoting hair growth comprises hinoki oil, red clover extract, and a peptide. The hinoki oil can comprise from about 0.01% to about 5% by weight of the composition, the red clover extract can comprise from about 1 ppmw to about 1,000 ppmw of the composition, and the peptide can comprise from about 0.01 ppmw to about 500 ppmw of the composition.

17 Claims, No Drawings

HAIR LOSS COMPOSITIONS AND METHODS OF MAKING AND USING SAME

CROSS REFERENCE TO RELATED APPLICATIONS

This application is a filing under 35 U.S.C. 371 of International Application No. PCT/US2014/013631 filed Jan. 29, 2014, entitled "Hair Loss Treatment Compositions and Methods of Making and Using Same," which claims priority to Provisional Application No. 61/758,618 filed Jan. 30, 2013, which applications are incorporated by reference herein in their entirety.

BACKGROUND

This disclosure relates to methods of hair loss treatment. More specifically, it relates to compositions and methods for inhibiting hair loss and/or stimulating hair growth.

Hair loss, also known as alopecia, affects both males and females, and may be caused by genetic factors, auto-immune disorders, chemotherapy, aging, local or systemic disease, etc. None of the conditions causing alopecia are very well understood, however such conditions are generally distressing to the individual experiencing them, in part due to the human physical appearance often being regarded as an essential factor in social communication and interactions. Consequently, some individuals experiencing alopecia can perceive hair loss as a social handicap.

Alopecia may occur in various parts of the human body, such as scalp, face, limbs, and trunk, and may be generally grouped in the following categories: male or female pattern baldness (e.g., androgenic alopecia), toxic alopecia (e.g., hair loss due to chemotherapy), alopecia aerata (i.e., hair loss occurs in demarcated areas), and scarring alopecia (e.g., hair loss due to inflammation and tissue destruction). Androgenic alopecia is one of the most common causes of hair loss and it occurs due to a deficiency in androgenic metabolism, e.g., accumulation of dihydrotestosterone (DHT) in hair follicles owed to a defective regulation in an enzyme responsible for DHT synthesis, 5α-reductase. Some current hair loss treatments involve the use of 5α-reductase inhibitors for modulating the levels of DHT in the hair follicles. However, such 5α-reductase inhibitors result only in moderate regrowth of hair in less than half of the users.

Some hair loss treatment formulations involve the use of an alcohol-based delivery vehicle, which may pose various problems. Before the hair loss treatment becomes effective, the alcohol present in the hair treatment formulation may cause the hair of the individual using it to become brittle, break and/or fall out. Alcohol based delivery vehicles may also lead to the irritation of the scalp, and as a result some people may discontinue the use before seeing the potential beneficial effects from the hair loss treatment.

As such, there exists a need for improved hair loss treatment compositions and methods of using same.

SUMMARY

In an embodiment, a composition for promoting hair growth comprises hinoki oil, red clover extract, and a peptide. The hinoki oil may comprise from about 0.01% to about 5% by weight of the composition, the red clover extract may comprise from about 1 ppmw to about 1,000 ppmw of the composition, and/or the peptide may comprise from about 0.01 ppmw to about 500 ppmw of the composition. The red clover extract may comprise an isoflavone, and the isoflavone may comprise biochanin A. The peptide may comprise at least one peptide selected from the group consisting of: Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, Acetyl Tetrapetide-2, and Myristoyl Pentapeptide-17, and in some embodiments, the peptide may be acetyl tetrapeptide-3. In an embodiment, the red clover extract comprises biochanin A, the peptide comprises acetyl tetrapeptide-3, the hinoki oil comprises from about 0.01% to about 1% by weight of the composition, the red clover extract comprises from about 5 ppmw to about 100 ppmw of the composition, and the acetyl tetrapeptide-3 comprises from about 0.05 ppmw to about 10 ppmw by weight of the composition. The composition may also include a carrier fluid, and the carrier fluid may be an alcohol free carrier fluid.

In an embodiment, a composition for promoting hair growth comprises an extract of *chamaecyparis obtusa*, wherein the extract of *chamaecyparis obtusa* is present in an amount ranging from about 0.01% to about 5% be weight, an isoflavone, wherein the isoflavone is present in an amount ranging from about 1 ppmw to about 500 ppmw, and a peptide, wherein the peptide is present in an amount ranging from about 0.01 ppmw to about 100 ppmw. The isoflavone may comprise an O-methylated isoflavone, and the O-methylated isoflavone may comprise at least one compound selected from the group consisting of: biochanin A, calycosin, formononetin, pratensein, and any combination thereof. In an embodiment, the isoflavone comprises biochanin-A. The peptide may comprise a tetrapeptide, and the tetrapeptide may comprise acetyl tetrapeptide-3. The peptide may be represented by the formula: A-X-Gly-His-Lys-Y, where A may comprise a monocarboxylic acid, where X may represent 1 to 3 Lys residues, and where Y may represent an —OH or —NH$_2$ group. The monocarboxylic acid may be represented by the formula: HOOC—R, where R may comprise a linear or branched $C_1$-$C_{24}$ aliphatic radical. The composition may be in the form of at least one of a shampoo, a conditioner, or a foamed liquid.

In an embodiment, a method for the treatment, prevention or management of a skin or hair condition, comprises administering to a subject in need thereof a therapeutically effective amount of a composition comprising hinoki oil, red clover extract, and a peptide. The hinoki oil may comprise from about 0.01% to about 5% by weight of the composition. The red clover extract may comprise from about 1 ppmw to about 1,000 ppmw of the composition. The peptide may comprise from about 0.01 ppmw to about 100 ppmw of the composition. The red clover extract may comprise an isoflavone, and the isoflavone may comprise biochanin A. The peptide may comprise at least one peptide selected from the group consisting of: Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, Acetyl Tetrapetide-2, and Myristoyl Pentapeptide-17. In an embodiment, the peptide is acetyl tetrapeptide-3. The composition may also include a carrier fluid, and the carrier fluid may be an alcohol free carrier fluid. In an embodiment, the subject is a human and the condition is alopecia.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

Hair is composed of a strong structural protein called keratin. Hair forms in a pouch-like structure below the skin called a hair follicle, which encloses the hair root. Visible hair, such as scalp hair for example, is the hair shaft, which is keratinized, hardened tissue that grows from the hair follicle. At the base of the follicle is the dermal papilla. The dermal papilla is fed by the bloodstream which carries nourishment to produce new hair. The dermal papilla plays a crucial role in the dermal-epidermal interactions and is of great importance for the hair formation and growth cycle.

The growth and development of hair follicles is influenced by a number of different growth factors and cytokines, such as members of the fibroblast growth factor (FGF) family and endothelial growth factors (EGF) family, e.g., vascular endothelial growth factor (VEGF).

Throughout the life of an individual, hair growth and hair renewal are determined by the activity of the hair follicles. Normal hair follicles cycle between a growth stage (anagen), a degenerative stage (catagen), and a resting stage (telogen), which are each characterized by very specific molecular and cellular mechanisms. Scalp hairs have a relatively long life cycle: the anagen stage ranges from 2 to 6 years, the catagen stage ranges from a few days to a few weeks, and the telogen stage is approximately three months. Shorter hairs found elsewhere on the human body have corresponding shorter anagen durations. The morphology of the hair and the hair follicle changes dramatically over the course of the life cycle of the hair.

During the anagen phase the hair follicle is highly active metabolically. The follicle comprises a dermal papilla at the base of the follicle; and epidermal matrix cells surrounding the dermal papilla form the base of the hair shaft, which extends upwards from the papilla through the hair canal. The matrix cells are the actively growing portion of the hair. The cells of the dermal papilla "send" signals to the matrix cells, which then migrate to the hair follicle matrix. In this region, the cells of the dermal papilla emit additional signals which allow the matrix cells to proliferate and then to differentiate, further allowing the elongation of the hair shaft. During the anagen phase, the hair follicle migrates through the dermis so as to be anchored in the hypodermis in contact with the adipose tissue.

At catagen, the matrix cells retract from the papilla, and other degenerative changes occur. For example, the vessels and capillaries supplying blood and nutrients to the hair follicle shrivel and stop functioning. A column of epithelial cells pushes the keratinized proximal shaft of the hair upwards and cell death occurs within the follicle. The cells of the lower part of the hair follicle enter into apoptosis, thus allowing degeneration of the hair follicle. The hair shaft is then shed from the scalp or other part of the body as the hair follicle enters telogen, the resting stage of the hair growth cycle. Telogen is a lag phase characterized by inactivity of the hair follicle and loss of the hair before a further entry into the anagen phase.

Although hair follicle regulation and growth are not well understood, they represent dynamic processes of proliferation, differentiation, and cellular interactions during tissue morphogenesis. It is believed that hair follicles are formed only in the early stages of development and are not replaced. Thus, an increase in damaged or non-functioning hair follicles is generally associated with hair loss. It is further believed that hair growth may be restored to a dormant and/or damaged hair follicle, but may generally not be restored to a follicle that has fully ceased functioning (e.g., a follicle that has died).

Disclosed herein are embodiments of hair loss treatment compositions comprising hinoki oil, red clover extract, a peptide and a carrier base fluid. In an embodiment, the composition may be used for inhibiting scalp hair loss and/or stimulating scalp hair growth. In some embodiments, the composition may be used for inhibiting facial hair (e.g., eyelashes, eyebrows, etc.) loss and/or stimulating facial hair growth. In other embodiments, the composition may be used for inhibiting hair loss and/or stimulating hair growth in other body areas, e.g., limbs, trunk, etc. Hereinafter, the disclosure will collectively refer to the use of Compositions for the Treatment of Hair Loss, designated a CTHL, with the understanding that while a particular focus of the present disclosure is the treatment of the scalp, such focus is non-limiting and a CTHL of the type disclosed herein may be used in the treatment of hair loss on any applicable body area. The CTHLs may be applied/administered to the body and used to treat hair loss, for example providing for both the inhibition of hair loss and the stimulation of hair growth. Each of the components of the CTHL as well as methods of using same will be described in more detail herein.

In an embodiment, the CTHL comprises hinoki oil or any fraction or portion of the hinoki oil (e.g., one or more components of the hinoki oil). Hinoki oil or white cedar oil is an essential oil usually obtained by steam distillation of the wood from the tree *Chamaecyparis obtusa*, which is a white cedar or conifer from a cypress family native to northeast Asia.

Hinoki oil is believed to modulate the expression of VEGF, and an increased VEGF production may aid in providing higher blood flow to hair follicles by enhancing angiogenesis (i.e., blood vessel formation) in the areas surrounding the hair follicles. Without wishing to be limited by theory, VEGF is believed to be a positive regulator of hair growth, i.e., the higher the VEGF levels, the higher the number of blood vessels supplying the hair follicle, the more enhanced the hair growth effect.

In an embodiment, the hinoki oil may be included within the CTHL in any suitable and/or therapeutic amount. In an embodiment the hinoki oil of the type disclosed herein may be present within the CTHL in an amount of from about 0.01 wt. % to about 10 wt. %, alternatively from about 0.02 wt. % to about 5 wt. %, or alternatively from about 0.05 wt. % to about 0.4 wt. %, based on the total weight of the CTHL.

In an embodiment, the CTHL comprises red clover extract. Red clover (i.e., *Trifolium pratense*) is a perennial herb that commonly grows wild in meadows throughout Europe and Asia, and has now been naturalized to grow in North America. The red flowers at the end of the branched stems of the clover plants may be used for the preparation of red clover extracts with an elevated content of isoflavones (e.g., biochanin A, formononetin, genistein, genistin, daidzein, daidzin, pratensein, pectolinarigenin, calycosin, trifoside, etc.). Without wishing to be limited by theory, isoflavones or phytoestrogens are plant-based compounds that produce estrogen-like effects in the human body. Red clover is available in a variety of preparations, including teas, tinctures, tablets, capsules, liquid extracts, and red clover extracts standardized to specific isoflavone contents. Red clover extract with an elevated isoflavone content may be obtained by solvent extraction, where the solvent can be an alcohol such as ethanol.

In an embodiment, the red clover extract comprises isoflavones comprising O-methylated isoflavones. O-methylated isoflavones or methoxy isoflavones comprise isoflavones with methylations on hydroxyl (—OH) groups, i.e., methoxy (—OCH$_3$) groups. The presence of the methoxy groups has an effect on the solubility of the isoflavones, e.g., the O-methylated isoflavones are less soluble in water than the isoflavones with similar structure but lacking the methoxy groups. Such solubility effects on the isoflavones makes the O-methylated isoflavones good candidates for selective extraction through solvent extraction methods. Nonlimiting examples of O-methylated isoflavones suitable for use in this disclosure include biochanin A, calycosin, formononetin, pratensein, and the like, or combinations thereof.

In an embodiment, the red clover extract comprises isoflavones comprising biochanin A. Without wishing to be limited by theory, biochanin A is believed to negatively regulate dihydrotestosterone (DHT) levels, and consequently to positively regulate hair growth by inhibiting the activity of 5α-reductase, an enzyme responsible for converting testosterone to DHT. An increased level of DHT is associated with alopecia (i.e., hair loss) in men, and to some extent, in women. The inhibitory effect of biochanin A on 5α-reductase is described in more detail in J. Endocrinology (1995), volume 147(2), pages 295-302, which is incorporated by reference herein in its entirety.

In an embodiment, the red clover extract may be included within the CTHL in a suitable and/or therapeutic amount. In an embodiment the red clover extract of the type disclosed herein may be present within the CTHL in an amount of from about 0.1 ppmw to about 1,000 ppmw, alternatively from about 1 ppmw to about 500 ppmw, or alternatively from about 5 ppmw to about 250 ppmw, based on the total weight of the red clover extract.

In an embodiment, the CTHL comprises one or more peptides. While not intending to be limited by theory, a peptide may promote the production of proteins that form the matrix around the dermal papilla, e.g., extracellular matrix (ECM) proteins. ECM proteins around the dermal papilla generally favor better hair anchoring. A larger amount of ECM proteins around the dermal papilla may lead to an increased size of the hair follicle, and thus may lead to an increase in hair number and vitality. In a further embodiment, the peptide may reduce inflammation of the scalp.

Nonlimiting examples of peptides suitable for use in this disclosure include tripeptide-1, acetyl hexapeptide-8, acetyl dipeptide-1, caproyl tetrapeptide-3, carnosine, glutathione, marine oligopeptide, palmitoyl oligopeptide, human oligopeptide-1 (EGF), acetyl tetrapeptide-3, palmitoyl tetrapeptide-7, acetyl tetrapeptide-5, palmitoyl hexapeptide-14, pentapeptide-3, nonapeptide-1, acetyl hexapeptide, hexapeptide-11, SH-polypeptide-15, hexanoyl dipeptide-3, acetyl octapeptide-3, palmitoyl tripeptide-5, palmitoyl dipeptide-5, palmitoyl dipeptide-6, acetyl tetrapetide-2, and myristoyl pentapeptide-17, a peptide compound characterized by Formula I and/or a peptide conjugate compound characterized by Formula II, or combinations thereof:

$$X\text{-Gly-His-Lys-Y} \qquad \text{Formula I}$$

$$A\text{-X-Gly-His-Lys-Y} \qquad \text{Formula II}$$

where A represents the radical corresponding to a monocarboxylic acid of general formula R—COOH, where R represents a linear or branched $C_1$-$C_{24}$ aliphatic radical optionally substituted with a hydroxyl group. In an embodiment, such monocarboxylic acid is unsaturated. In an embodiment, the monocarboxylic acid comprises lipoic acid or its reduced form, dihydrolipoic acid, N-lipoyl lysine, retinoic acid, or combinations thereof. X represents 1 to 3 Lys residues, that are optionally methylated. In the case of Formula II, X may represent a covalent bond. Y represents a hydroxyl (i.e., —OH) or amino (i.e., —NH$_2$) group. The amino acids of Formulas I and II may be in the D, L or DL form. A-X may represent a hydrogen atom.

In an embodiment, the monocarboxylic acid A comprises a polyunsaturated fatty acid, e.g., containing from 1 to 6 unsaturations. In an embodiment, the monocarboxylic acid A comprises an omega-3 acid comprising α-linolenic acid, cervonic acid, timnodonic acid, pinolenic acid, or combinations thereof. Cervonic acid, timnodonic acid and pinolenic acid are also known under the respective names: 4,7,10,13, 16,19-docosahexaenoic acid (DHA), 5,8,11,14,17-eicosapentaenoic acid (EPA) and 5,9,12-octodecatrienoic acid. Alternatively, in an embodiment, the monocarboxylic acid A comprises acetic acid, myristic acid, palmitic acid, hydroxydecenoic acids, decenoic acids, trans-10-hydroxy-Δ2-decenoic acid, trans-oxo-9-decen-2-oic acid, or combinations thereof.

In an embodiment, the peptide compounds characterized by Formulas I and/or II may be chemically or physically conjugated with the monocarboxylic acids A. The conjugated peptides may be bonded in the form of salts, esters, or amides to such monocarboxylic acids A. The amino acids in the peptides characterized by Formula I or the peptide conjugates characterized by Formula II may have a D, L, or DL configuration, i.e., such peptides may contain one or more asymmetrical carbon atoms, and thus may exist in the form of enantiomers, diastereoisomers, or combinations thereof. The peptide conjugates characterized by Formula II are low-molecular-weight derivatives which may be obtained in the form of amides of the monocarboxylic acids A.

In an additional embodiment, the peptides characterized by Formula I or the peptide conjugates characterized by Formula II may be coupled with zinc, in the form of salts, so as to form complexes.

For the purposes of the present disclosure, the term "Lys" is intended to mean lysine or a halogenated derivative of lysine, such as dihydrobromomethyllysine, the term "His" is intended to mean histidine, and the term "Gly" is intended to mean glycine or an alkylated derivative thereof, such as methylglycine.

In an embodiment, the peptides characterized by Formula I or the peptide conjugates characterized by Formula II may be obtained in the $NH_2$-terminal form (e.g., exhibiting an amide function), alternatively in the OH-terminal form (e.g., exhibiting a carboxylic acid function). Examples of peptides and peptide conjugates suitable for use in the present disclosure are described in more detail in U.S. Pat. No. 7,507,719 to Pinel et al. and U.S. Pat. No. 8,227,426 to Gupta et al., each of which is incorporated by reference herein in its entirety.

In an embodiment, the peptide may be included within the CTHL in a suitable and/or therapeutic amount. In an embodiment, the peptide may comprise acetyl tetrapeptide-3. In an embodiment the peptide of the type disclosed herein may be present within the CTHL in an amount of from about 0.01 ppmw to about 1,000 ppmw, alternatively from about 0.01 ppmw to about 500 ppmw, or alternatively from about 0.1 ppmw to about 100 ppmw, based on the total weight of the CTHL.

In an embodiment, the CTHL may further comprise retinyl palmitate. Retinyl (or retinol) palmitate, or vitamin A palmitate, is the ester of retinol (vitamin A) and palmitic acid, and is commonly used as a vitamin supplement for the treatment of vitamin A deficiency. Retinyl palmitate may act as an antioxidant, potentially limiting the free radical damage to the skin and scalp.

In an embodiment, the retinyl palmitate may be included within the CTHL in a suitable and/or therapeutic amount. In an embodiment the retinyl palmitate may be present within the CTHL in an amount of from about 0.01 wt. % to about 0.5 wt. %, alternatively from about 0.05 wt. % to about 0.2 wt. %, or alternatively from about 0.05 wt. % to about 0.1 wt. %, based on the total weight of the CTHL.

In an embodiment, the carrier base fluids that may be used in the CTHL include any carrier fluid or combination of excipients suitable for use in cosmetic and/or medicinal applications. For example, the CTSHL may comprise an aqueous carrier base fluid. In an embodiment, the aqueous carrier base fluid comprises deionized water.

In an embodiment, the carrier base fluid is substantially free of alcohol, i.e., an alcohol-free carrier base fluid. In such embodiment, the carrier base fluid may comprise less than about 5%, less than about 4%, less than about 3%, less than about 2%, less than about 1%, less than about 0.1%, less than about 0.01%, less than about 0.001%, or less than about 0.0001 wt. % alcohol. In an embodiment, the alcohol refers to denatured alcohol (e.g., comprising ethanol).

In an embodiment, the carrier base fluid may act as a solvent, carrier, diluent and/or dispersant for the constituents of the composition, and may allow for the uniform application of the constituents to the surface of the skin at an appropriate dilution, e.g., topical application. For example, carrier base fluids can be emulsions, lotions, creams, tonics, sprays, aerosols, and the like. The carrier base fluid may also facilitate penetration of the composition into the skin.

In an embodiment, the carrier base fluid comprises a lotion suitable for topical application. In such embodiment, the lotion may comprise carbomer, water, glycerin, isopropyl myristate, mineral oil, stearic acid, glycol stearate, cetyl alcohol, dimethicone, preservatives, triethanolamine, and the like, or combinations thereof.

Alternatively, in an embodiment, the carrier base fluid comprises a gel suitable for topical application. In such embodiment, the gel may comprise water, carbomer, glycerin, propylene glycol, preservatives, and the like, or combinations thereof.

The various ingredients used in the CTHL may be soluble or insoluble in the carrier base fluid. In an embodiment, all ingredients of a CTHL are soluble in the carrier base fluid, and the carrier base fluid acts as a solvent. In another embodiment, one or more of the ingredients used in the CTHL may be solubilized in a solubilizer prior to mixing in the carrier base fluid, such that these ingredients become soluble in the carrier base fluid. Nonlimiting examples of solubilizers suitable for use in the present disclosure include water, glycerin (e.g., vegetable glycerin), various esters, polyethylene glycol (PEG), derivatives thereof, or combinations thereof.

Alternatively, in an embodiment, all or some ingredients of a CTHL may be insoluble in the carrier base fluid. In such embodiment, those ingredients may be dispersed as a first step in a vehicle by means of, for example, a suspension, emulsion, gel, cream or paste, or the like, followed by a second step of introducing the vehicle into the carrier base fluid. Nonlimiting examples of vehicles suitable for use in the present disclosure include water, denatured alcohol, propylene carbonate, PEG, castor oil, ethylene glycol monobutyl ether, diethylene glycol monoethyl ether, corn oil, dimethyl sulfoxide, ethylene glycol, isopropanol, wild soybean (e.g., *Glycine soja*) oil, sorbitol, soluble collagen, butylene glycol, glycerin (e.g., vegetable glycerin), or combinations thereof, or other suitable various solvents that aid in penetration of the skin. Vehicles or carrier base fluids suitable for use in the present disclosure are described in more detail in U.S. Pat. No. 6,184,247 to Scheider and U.S. Pat. No. 6,579,516 to Mansouri, each of which is incorporated by reference herein in its entirety. It will be apparent to one of skill in the art, with the help of this disclosure, that the range of possible acceptable vehicles and carrier base fluids is very broad. In an embodiment, the vehicle may be present in an amount of from about 0.1 wt. % to about 10 wt. %, alternatively from about 1 wt. % to about 7 wt. %, or alternatively from about 4 wt. % to about 5 wt. %, based on the total weight of the CTHL.

The carrier base fluid may be present in an amount of from about 90 wt. % to about 99.99 wt. %, alternatively from about 92 wt. % to about 97 wt. %, or alternatively from about 94 wt. % to about 95 wt. %, based on the total weight of the CTHL. Alternatively, the carrier base fluid may comprise the balance of the CTHL after considering the amount of the other components used.

In an embodiment, the CTHL may optionally comprise one or more additives or additional components/ingredients, as may be suitable depending upon the end use of the CTHL. The CTHL may comprise various known and conventional cosmetic adjuvants so long as they do not detrimentally affect the desired hair loss preventative or hair growth/regrowth stimulatory properties of the composition. In an embodiment, the CTHL may further comprise inactive ingredients, such as surfactants, co-solvents, and excipients or fillers (e.g., solid, semi-solid, liquid, etc.); emollients; delivery enhancers; circulation enhancers; antimicrobial agents; anti-inflammatory agents; foaming agents; carriers; diluents; binding agents (e.g., dextran); thickening agents;

gelling agents; vitamins, retinoids, and retinols (e.g., vitamin B3, vitamin A, etc.); pigments; fragrances; sunscreens and sunblocks; anti-oxidants and radical scavengers (e.g., tocopheryl acetate or vitamin E acetate); organic hydroxy acids; exfoliants; skin conditioners (e.g., ethylhexylglycerin, hydrolyzed soy protein, glycol distearate, cyclopentasiloxane, quaternium-79 hydrolyzed keratin, propylene glycol, etc.); moisturizers; humectants (e.g., hydrolyzed soy protein, propylene glycol, etc.); ceramides, pseudoceramides; phospholipids, sphingolipids, cholesterol, glucosamine; pharmaceutically acceptable penetrating agents (e.g., n-decylmethyl sulfoxide, lecithin organogels, tyrosine, lysine, etc.); preservatives (e.g., phenoxyethanol, benzoic acid, dehydroacetic acid, polyaminopropyl biguanide, DMDM hydantoin or 1,3-bis(hydroxymethyl)-5,5-dimethylimidazolidine-2,4-dione, iodopropynyl butylcarbamate, iodopropynyl butylcarbonate, stearalkonium chloride, etc.); amino acids such as proline; pyrrolidone carboxylic acid, its derivatives and salts; saccharide isomerate; panthenol (i.e., provitamin of $B_5$); buffers together with a base such as triethanolamine or sodium hydroxide; waxes, such as beeswax, ozokerite wax, paraffin wax; plant extracts, obtained from plants such as Aloe vera leaf, cornflower, witch hazel, elderflower, green tea (e.g., *Camellia sinensis*) leaf, grape (e.g., *Vitis vinifera*) seed, jojoba (e.g., *Simmondsia chinensis*) seed, tea tree (e.g., *Malaleuca alternifolia*) leaf, rosemary (e.g., *Rosmarinus officinalis*), henna, sunflower (e.g., *Helianthus annuus*) seed, wild soybean (e.g., *Glycine soja*), argan tree kernel or argan, cucumber, shiso, etc.; or combinations thereof. As will be appreciated by one of skill in the art viewing this disclosure, the amount of optional ingredients may be varied depending upon the intended application of the CTHL, and in various embodiments a suitable and/or therapeutic amount may be included in the CTHL.

In an embodiment, the plant extracts used in the CTHLs may be obtained from any commercially available source. For example, hinoki oil, tea tree oil, and rosemary oil may be purchased from Liberty Natural Products of Oregon City, Ore., and grape seed oil may be purchased from MakingCosmetics Inc. of Renton, Wash.

Alternatively, in an embodiment, the plant extracts used in the CTHLs may be obtained using any suitable known extraction method. For example, in an embodiment, a plant extract (e.g., green tea extract, red clover extract, etc.) can be produced/obtained by extracting a plant or a plant portion (e.g., leaf, flower, stem, etc.) with an organic solvent. Nonlimiting examples of organic solvents suitable for use in the present disclosure include hexane, ethyl acetate, ethanol, hydro-ethanol, denatured alcohol, and the like, or combinations thereof.

Alternatively, in an embodiment, a plant extract may be produced by solvent sequential fractionation. For example, by using this technique, a plant or plant portion (e.g., leaves and stems of a shiso plant) may be sequentially extracted with hexane, ethyl acetate, ethanol, and hydro-ethanol. The extracts obtained after each step (i.e., fractions) of the sequence will contain chemical compounds in increasing order of polarity, similarly to the solvents used for extracting them, e.g., the least polar compounds will be extracted in hexane, followed by ethyl acetate, and the most polar compounds will be extracted in hydro-ethanol. Without wishing to be limited by theory, hydro-ethanol is a mixture of ethanol and water, which has a higher polarity than ethanol due to the fact that it contains water, which is inherently more polar than ethanol. The fractions produced by solvent sequential fractionation may be dried to evaporate the solvents, resulting in a plant extract (e.g., shiso extract). It will be apparent to those of skill in the art with the help of this disclosure that many other solvents can be used in practicing the solvent sequential fractionation extraction of any of the plant extracts used in the CTHLs.

Alternatively, in an embodiment, a plant extract may be produced by total solvent extraction techniques (e.g., total hydro-ethanolic extraction techniques). Generally, this technique may be referred to as a lump-sum extraction of a material of interest, for example lump-sum extraction of red clover leaves. The extract generated by total solvent extraction techniques may contain a broad variety of phytochemicals present in the material to be extracted, including fat soluble compounds and water soluble compounds. Following collection of the plant extract, the solvent (e.g., hexane, ethyl acetate, hydro-ethanol, etc.) may be evaporated, resulting in an extract that may be used in the CTHLs.

Alternatively, in an embodiment, a plant extract may be produced by total ethanol extraction. This technique also uses plant material to obtain the extract of interest, but ethanol, rather than hydro-ethanol, is the solvent. This extraction technique generates an extract that may include fat soluble and/or lipophilic compounds in addition to water soluble compounds. Following collection of the plant extract, the solvent (e.g., ethanol) may be evaporated, resulting in an extract that may be used in the CTHLs.

Alternatively, in an embodiment, a plant extract may be produced by supercritical fluid carbon dioxide extraction (SFE). In this extraction procedure, a plant material containing an extract of interest is not exposed to any organic solvents. Rather, the extraction solvent is carbon dioxide, with or without a modifier, in supercritical conditions (e.g., a temperature higher than 31.3° C. and a pressure higher than 73.8 bar). It will be appreciated by those of skill in the art with the help of this disclosure that the temperature and pressure conditions may be varied to obtain the best yield of extract. SFE generally generates an extract of fat soluble and/or lipophilic compounds, similar to the total hexane and/or ethyl acetate extraction technique described previously herein.

It will be apparent to those of skill in the art with the help of this disclosure that there are many other suitable plant extraction processes that may be used to obtain the plant extracts to be used in the CTHLs.

In an embodiment, the CTHL comprises a surfactant. The surfactant may function to improve the compatibility of the CTHL components or ingredients with each other. Nonlimiting examples of surfactants suitable for use in the present disclosure include polyethoxylated PEG fatty acids, PEG-fatty acid diesters, PEG-fatty acid mono- and di-ester mixtures, PEG-40 castor oil, PEG-35-200 castor oil, PEG-35-200 hydrogenated castor oil, PEG-10-80, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, polysaccharide esters, hydroxypropyl methylcellulose, polyethylene glycol alkyl phenols, polyoxyethylene-polyoxypropylene block copolymers, sorbitan fatty acid esters, sorbitan laurate, polysorbate 20, decyl glucoside, lower alcohol fatty acid esters, ceteareth-20-40, ianeth-20-40, poloxamer 105-407, steareth-21-100, cocamidopropyl betaine, cocamidopropyl hydroxysultaine, disodium cocamido MIPA-sulfosuccinate, sodium cocoyl isethionate, disodium lauryl sulfosuccinate, sodium lauroampho hydroxypropylsulfate, stearalkonium chloride, ionic surfactants, and the like, and combinations thereof.

The inclusion of a surfactant may be useful in providing the CTHL in the form of a shampoo or other similar cleansing product.

In an embodiment, the CTHL comprises a co-solvent. The co-solvent may function to improve the solubility of certain ingredients in the CTHL. Nonlimiting examples of co-solvents suitable for use in the present disclosure include alcohols, polyols, polyethylene glycols ethers, amides, esters, and the like, or combinations thereof. In some embodiments, a co-solvent may be present, but may not comprise an alcohol. Such embodiments may be useful in providing the CTHL in an alcohol free form.

In an embodiment, the CTHL comprises an excipient. Without wishing to be limited by theory, an excipient may be generally defined as a pharmacologically inactive substance used in the formulation or composition of a medication. For the purposes of this disclosure an excipient may be a substance or compound that might not affect the hair loss and/or hair regrowth process. Nonlimiting examples of excipients suitable for use in the present disclosure include colorants or dyes (e.g., FD&C red 40), antioxidants, preservatives, chelating agents, viscomodulators, tonicifiers, odorants, opacifiers, suspending agents, binders, and the like, or combinations thereof.

In an embodiment, the CTHL comprises an emollient. The emollient may function to improve the hydration (e.g., water content) of the skin by reducing evaporation. Nonlimiting examples of emollients suitable for use in the present disclosure include butane-1,3-diol; cetyl palmitate; dimethylpolysiloxane; cyclopentasiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; dimethiconol; wild soybean oil; sesame oil; coconut oil; safflower oil; isoamyl laurate; nonoxynol-9; panthenol; hydrogenated vegetable oil; cetearyl alcohol; tocopheryl acetate; tocopheryl linoleate; allantoin; propylene glycol; glycol distearate, which may be of vegetable origin; arachis oil; castor oil; isostearic acid; palmitic acid; isopropyl linoleate; myristyl lactate; and the like, or combinations thereof.

In an embodiment, the CTHL comprises a delivery enhancer. The delivery enhancer may function to promote diffusion across stratum corneum (i.e., the outermost layer of skin/epidermis), for example to enhance the transdermal delivery of the ingredients of the CTHL. Nonlimiting examples of delivery enhancers suitable for use in the present disclosure include polyethylene glycol monolaurate; alkyl lactams; long chain amides; substituted 1,2-dioxacyclopentanes; substituted 1,3-diacyclohexanes; 1,4:3,6 dianhydro-2,5-di-o-methyl-D-glucitol; and the like, or combinations thereof.

In an embodiment, the CTHL comprises a circulation enhancer. The circulation enhancer may function to increase blood flow circulation to the cells of the scalp, which may in turn increase health of the cutaneous and subcutaneous tissue of the scalp. The circulation enhancers are also believed to aid in the delivery and penetration of the ingredients of the CTHL as well. Nonlimiting examples of circulation enhancers suitable for use in the present disclosure include thistle, ginkgo biloba, peppers (e.g., cayenne and red peppers), ursolic acid, and the like, or combinations thereof.

In an embodiment, the CTHL comprises an antimicrobial agent. The antimicrobial agent may function to help reduce the activities of micro-organisms on skin or body. Nonlimiting examples of antimicrobial agents suitable for use in the present disclosure include organic solvents, (e.g., alcohols), natural oils or extracts (e.g., oil of wintergreen, peppermint oil, etc.), ursolic acid, triclosan, parabens, and the like, or combinations thereof.

In an embodiment, the CTHL comprises an anti-inflamatory agent. The anti-inflamatory agent may function to decrease and counter the inflammation surrounding hair follicles. It is believed that in patterned alopecia, for example, there is a chronic inflammatory process, subtending to the hair bulbs, which may lead to eventual scarring of the lower part of the hair follicle, making regrowth unlikely if not impossible. Nonlimiting examples of anti-inflamatory agents suitable for use in the present disclosure include steroidal anti-inflammatories, non-steroidal anti-inflammatories, corticosteroids, ibuprofen, aspirin, Aloe vera, shiso extract, ximenynic acid, *Glycyrrhiza inflata* root extract, amentoflavone, boswellia, luteolin, derivatives thereof, and the like, or combinations thereof.

As will be apparent to one of skill in the art, with the help of this disclosure, other suitable ingredients/components may be used in the CTHL, and each ingredient/component of the CTHL may perform more than one function (e.g., ursolic acid may be a circulation enhancer as well as an antimicrobial agent).

In an embodiment, the CTHL may be prepared via any suitable method or process. The components of the CTHL (e.g., hinoki oil, red clover extract, peptide, carrier base fluid, optional ingredients) may be combined using any mixing device compatible with the composition.

Alternatively, in an embodiment, some of the components of the CTHL may be mixed in the form of a concentrate which may be mixed at a later time with the rest of the components of the CHTL, i.e., diluent. Such concentrate may comprise hinoki oil, red clover extract, peptide, carrier base fluid, and any suitable optional ingredients. In an embodiment, the concentrate may have a 100×, alternatively 50×, alternatively 25×, alternatively 10×, alternatively 5×, alternatively 2× concentration when reported to the concentration of the same components in the final CTHL. For example, if the concentrate has a 10× concentration, in order to obtain the final CTHL, 1 part of concentrate would be mixed with 9 parts of the diluent, using any mixing device compatible with the composition, resulting in a final CTHL with a 1× concentration.

Various additional embodiments can include, but are not limited to:

In an embodiment, the CTHL comprises hinoki oil, red clover extract, peptide, carrier base fluid, optional ingredients, and may be intended for use as a scalp stimulator, for example a foaming scalp stimulator. For example, the CTHL may comprise about 0.1 wt. % to about 0.3 wt. % hinoki oil, about 1 ppmw to about 500 ppmw red clover extract, about 0.01 to about 100 ppmw acetyl tetrapeptide-3, along with retinyl palmitate, water, polysorbate 20, glycerin, panthenol, allantoin, cocamidopropyl betaine, hydroxypropyl methylcellulose, grape seed oil, tea tree leaf oil, rosemary oil, dextran, butylene glycol, phenoxyethanol, benzoic acid, dehydroacetic acid, ethylhexyl glycerin, and/or polyaminopropyl biguanide, where the wt. % are based on the total weight of the CTHL.

In an embodiment, the CTHL comprises hinoki oil, red clover extract, peptide, carrier base fluid, optional ingredients, and may be intended for use as a shampoo. For example, the CTHL may comprise about 0.1 wt. % to about 2.5 wt. % hinoki oil, about 1 ppmw to about 500 ppmw red clover extract, about 0.01 ppmw to about 500 ppmw acetyl tetrapeptide-3, about 0.05 wt. % retinyl palmitate, deionized water, green tea leaf extract, Aloe vera leaf extract, natural henna extract, hydrolyzed soy protein, glycol distearate of vegetable origin, DMDM hydantoin, iodopropynyl butylcarbonate, vegetable glycerin, hydroxypropyltrimonium chloride, sodium cocoyl isethionate, cocamidopropyl hydroxysultaine, cocamide MIPA, disodium lauryl sulfosuccinate, sodium lauroampho hydroxypropylsulfate, decyl glucoside, cocamidopropyl betaine, cyclopentasiloxane, dimethiconol, sunflower seed oil, wild soybean oil, tocopheryl acetate, quaternium-79 hydrolyzed keratin, FD&C red 40, and/or fragrance, where the wt. % are based on the total weight of the CTHL.

In an embodiment, the CTHL comprises hinoki oil, red clover extract, peptide, carrier base fluid, optional ingredients, and may be intended for use as a conditioner. For example, the CTHL may comprise 0.2 wt. % hinoki oil, 1 ppmw to about 500 ppmw red clover extract, about 0.01 ppmw to about 500 ppmw acetyl tetrapeptide-3, 0.1 wt. % retinyl palmitate, deionized water, Aloe vera leaf extract, green tea leaf extract, jojoba seed oil, cetearyl alcohol, vegetable glycerin, PEG-40 castor oil, propylene glycol, DMDM hydantoin, iodopropynyl butylcarbonate, stearalkonium chloride, panthenol, argon oil, cyclopentasiloxane, dimethiconol, wild soybean oil, tocopheryl acetate, hydrolyzed soy protein, polysorbate 20, and fragrance, where the wt. % are based on the total weight of the CTHL.

In an embodiment, a method for treating hair loss comprises topical application of the CTHL on the scalp or any other body area where hair growth or regrowth is desirable. The CTHLs may be useful for treating hair loss by preventing or slowing hair loss and/or stimulating or increasing hair growth or regrowth. The CTHLs described herein may be useful in a wide variety of finished products, including pharmaceutical products and cosmetic products. The CTHLs may be prepared, packaged, and labeled for modulation of hair growth or regrowth, and for diminishing the hair loss process.

In an embodiment, the CTHLs disclosed herein may be topically administered in the form of a solution, gel, lotion, cream, ointment, oil-in-water emulsion, water-in-oil emulsion, stick, spray, aerosol, paste, mousse, tonic, liposome or other cosmetically and topically suitable form. In an embodiment, the CTHLs may be topically applied to an area to be treated, for example the scalp in humans, by spraying, dabbing, swabbing, rubbing, or combinations thereof.

In an embodiment, the CTHL may be topically applied in the form of a scalp stimulator foam. In another embodiment, the CTHL may be topically dispersed on the scalp in an aerosol form such as in a chlorofluorocarbon solvent, for delivery in spray form. The spray form may present some advantages including high loading, enhanced drug uptake, convenient application, and less matting the hair in the region of application. In such embodiments, the CTHL may remain on the scalp for a period of time of about 1 week, alternatively about 1 day, alternatively about 12 h, alternatively about 4 h, alternatively about 1 h, alternatively about 30 min, alternatively about 5 min, or alternatively about 1 min. The CTHL may be removed at any desired point in time by washing and/or rinsing the scalp.

In an alternative embodiment, the CTHL may be topically applied in the form of a shampoo, conditioner, or any other suitable hair care product formulation, or combinations thereof. In such embodiment, the shampoo or conditioner may be rinsed after application, for example, immediately after the application, alternatively after a period of time of about 5 s, alternatively about 30 s, alternatively about 1 min, alternatively about 5 min, alternatively about 30 min, alternatively about 1 h, alternatively about 4 h, alternatively about 12 h, or alternatively about 24 h. In an embodiment, the conditioner may be the "leave-in" type conditioner, e.g., the conditioner may be left on the scalp without rinsing until the next scalp washing. In an embodiment, more than one form of CTHL may be applied to the hair, for example, in one treatment session, alternatively in different treatment sessions, the CTHL may be topically applied to the scalp as a shampoo, conditioner, scalp stimulator foam, or combinations thereof.

The CTHLs may be added in a CTHL concentrate form as previously described herein to any shampoo, conditioner, styling product, or any other suitable hair care formulation that is commercially available or commonly used. For example, a CTHL concentrate may be mixed with fatty acid esters or sorbitol and sorbitol anhydrides (e.g., polysorbates). These compounds have nonionic properties that inhibit shedding of hair. Without wishing to be limited by theory, polysorbates are nonionic surfactants obtained by esterification of sorbitol with one or three molecules of a fatty acid (e.g. stearic, lauric, oleic, palmitic, etc.).

In an embodiment, the CTHL may be topically administered at least on a daily, and preferably a twice daily, basis for a period of time sufficient to bring about the desired level of improvement in modulation of hair growth or regrowth. For example, a user may topically administer the CTHL directly to a balding area or other area where increased hair growth is desired by gently massaging the composition of the present invention into the desired area. This process may be repeated later the same day. In an embodiment, the CTHL may be left on the scalp or other area where increased hair growth is desired between applications occurring on the same day or on different days. As will be appreciated by one skilled in the art with the help of this disclosure, when the CTHLs may be topically applied/administered periodically on a routine basis prior to, during, and subsequent to modulation of hair growth or regrowth. Generally, the CTHLs may be topically administered on a daily basis, although more frequent applications also may be used.

In an embodiment, the topical application of the CTHL may continue for any suitable period of time. For example, within a few weeks to a few months of the initial application, a user may notice a reduction in hair loss and/or an increase in hair growth or regrowth. It should be appreciated that the frequency with which the CTHL should be applied will vary depending on the desired effect. In particular, the degree of cosmetic enhancement might vary directly with the total amount of CTHL used.

In an embodiment, disclosed herein is a method of treating a skin or a hair condition comprising administering a composition to dermal papilla cells of a subject, wherein the composition comprises hinoki oil, red clover extract, and a peptide; and increasing a growth factor from the dermal papilla cells of the subject in response to administering the composition.

As will be appreciated by those of skill in the art with the help of this disclosure, other methods may be used to topically apply/administer the CTHLs described herein.

In an embodiment, a composition for the treatment of hair loss such as CTHL may be advantageously used to diminish hair loss and/or promote hair growth and/or regrowth. For example, as disclosed herein, a composition for the treatment of hair loss such as CTHL may diminish and/or stop hair loss in a time period of from about 7 days to about 80 days, alternatively from about 10 days to about 28 days, or alternatively from about 14 days to about 21 days.

While not intending to be limited by theory, it is believed that the CTHL may advantageously regrow hair in a time period of from about 4 weeks to about 20 weeks, alternatively from about 6 weeks to about 16 weeks, or alternatively from about 8 weeks to about 12 weeks.

In some embodiments, the CTHL may advantageously diminish and/or stop the itching of the scalp when a CTHL is topically applied to the scalp, which may be due in some embodiments to the use of an alcohol free carrier fluid along with one or more optional ingredients In an embodiment, the CTHL may advantageously promote hair growth from dormant and/or injured hair follicles, e.g., the CTHL may have a rejuvenating effect on the hair follicles. However, if the hair follicle is dead, it is believed that the hair follicle cannot become functional again. Additional advantages of the CTHL and methods of using same may be apparent to one of skill in the art viewing this disclosure.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

90-Day Trial

A 90-day trial of an embodiment of the composition described herein was conducted for twelve (12) participants. The composition comprised hinoki oil, red clover extract, and a peptide. For each participant, blood values were drawn at the beginning of the study to determine the hormone levels and identify any physiological imbalances. During the study, photos were taken every month on or around the 1st. Monthly assessments and interviews on hair loss reduction and hair regrowth, where applicable, were also conducted during the study. The participants purchased the composition including shampoo, conditioner, and scalp treatment and used it at least 3 times a week.

The study showed that eleven of the participants had reduction in 4-6 weeks of hair loss (e.g., noted decrease hair in shower, vanity or brush). One of the participants experienced exacerbation of their hair loss and opted to stop using the product during the study. Three participants exhibited evidence of new hair growth in areas of loss. Four participants noted thickening of the texture and feel of their hair. Overall, ten of the participants had positive experiences and continued to use the product 3-7 days a week past the end of the study period.

ADDITIONAL DISCLOSURE

The following are nonlimiting, specific embodiments in accordance with the present disclosure:

In a first embodiment, a composition for promoting hair growth comprises: hinoki oil; red clover extract; and a peptide.

A second embodiment may include the composition of the first embodiment, wherein the hinoki oil comprises from about 0.01% to about 5% by weight of the composition.

A third embodiment may include the composition of the first or second embodiment, wherein the red clover extract comprises from about 1 ppmw to about 1,000 ppmw of the composition.

A fourth embodiment may include the composition of any of the first to third embodiments, wherein the peptide comprises from about 0.01 ppmw to about 500 ppmw of the composition.

A fifth embodiment may include the composition of any of the first to fourth embodiments, wherein the red clover extract comprises an isoflavone.

A sixth embodiment may include the composition of the fifth embodiment, wherein the isoflavone comprises biochanin A.

A seventh embodiment may include the composition of any of the first to sixth embodiments, wherein the peptide comprises at least one peptide selected from the group consisting of: Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, Acetyl Tetrapetide-2, and Myristoyl Pentapeptide-17.

An eighth embodiment may include the composition of any of the first to seventh embodiments, wherein the peptide is acetyl tetrapeptide-3.

A ninth embodiment may include the composition of any of the first to eighth embodiments, wherein the red clover extract comprises biochanin A, wherein the peptide comprises acetyl tetrapeptide-3, wherein the hinoki oil comprises from about 0.01% to about 1% by weight of the composition, wherein the red clover extract comprises from about 5 ppmw to about 100 ppmw of the composition, and wherein the acetyl tetrapeptide-3 comprises from about 0.05 ppmw to about 10 ppmw by weight of the composition.

A tenth embodiment may include the composition of any of the first to ninth embodiments, wherein the composition further comprise a carrier fluid, and/or wherein the carrier fluid is an alcohol free carrier fluid.

In an eleventh embodiment, a composition for promoting hair growth, the composition comprising: an extract of *chamaecyparis obtusa*, wherein the extract of *chamaecyparis obtusa* is present in an amount ranging from about 0.01% to about 5% be weight; an isoflavone, wherein the isoflavone is present in an amount ranging from about 1 ppmw to about 500 ppmw; and a peptide, wherein the peptide is present in an amount ranging from about 0.01 ppmw to about 100 ppmw.

A twelfth embodiment may include the composition of the eleventh embodiment, wherein the isoflavone comprises an O-methylated isoflavone.

A thirteenth embodiment may include the composition of the twelfth embodiment, wherein the O-methylated isoflavone comprises at least one compound selected from the group consisting of: biochanin A, calycosin, formononetin, pratensein, and any combination thereof.

A fourteenth embodiment may include the composition of any of the eleventh to thirteenth embodiments, wherein the isoflavone comprises biochanin-A.

A fifteenth embodiment may include the composition of any of the eleventh to fourteenth embodiments, wherein the peptide comprises a tetrapeptide.

A sixteenth embodiment may include the composition of the fifteenth embodiment, wherein the tetrapeptide comprises acetyl tetrapeptide-3.

A seventeenth embodiment may include the composition of any of the eleventh to sixteenth embodiments, wherein the peptide is represented by the formula: A-X-Gly-His-Lys-Y, wherein A comprises a monocarboxylic acid, wherein X represents 1 to 3 Lys residues, and wherein Y represents an —OH or —NH$_2$ group.

An eighteenth embodiment may include the composition of the seventeenth embodiment, wherein the monocarboxylic acid is represented by the formula: HOOC—R, wherein R comprises a linear or branched $C_1$-$C_{24}$ aliphatic radical.

A nineteenth embodiment may include the composition of any of the eleventh to eighteenth embodiments, wherein the composition is in the form of at least one of a shampoo, a conditioner, or a foamed liquid.

In a twentieth embodiment, a method for the treatment, prevention or management of a skin or hair condition, comprising administering to a subject in need thereof a therapeutically effective amount of a composition comprising hinoki oil, red clover extract, and a peptide.

A twenty first embodiment may include the composition of the twentieth embodiment, wherein the hinoki oil comprises from about 0.01% to about 5% by weight of the composition.

A twenty second embodiment may include the composition of the twentieth or twenty first embodiment, wherein the red clover extract comprises from about 1 ppmw to about 1,000 ppmw of the composition.

A twenty third embodiment may include the composition of any of the twentieth to twenty second embodiments, wherein the peptide comprises from about 0.01 ppmw to about 100 ppmw of the composition.

A twenty fourth embodiment may include the composition of any of the twentieth to twenty third embodiments, wherein the red clover extract comprises an isoflavone.

A twenty fifth embodiment may include the composition of the twenty fourth embodiment, wherein the isoflavone comprises biochanin A.

A twenty sixth embodiment may include the composition of any of the twentieth to twenty fifth embodiments, wherein the peptide comprises at least one peptide selected from the group consisting of: Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, Acetyl Tetrapetide-2, and Myristoyl Pentapeptide-17.

A twenty seventh embodiment may include the composition of any of the twentieth to twenty sixth embodiments, wherein the peptide is acetyl tetrapeptide-3.

A twenty eighth embodiment may include the composition of any of the twentieth to twenty seventh embodiments, wherein the composition further comprise a carrier fluid, wherein the carrier fluid is an alcohol free carrier fluid.

A twenty ninth embodiment may include the composition of any of the twentieth to twenty eighth embodiments, wherein the subject is a human and the condition is alopecia.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of a reference in the Detailed Description of the Embodiments is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method for the treatment or management of alopecia, comprising administering to a subject having alopecia a therapeutically effective amount of a composition comprising:
   hinoki oil, where the hinoki oil comprises from about 0.02% to about 5% by weight of the composition;
   red clover extract comprising biochanin A, wherein the red clover extract comprises from about 0.1 ppmw to about 1000 ppmw of the composition; and
   a peptide, wherein the peptide comprises from about 0.01 ppmw to about 1000 ppwm by weight of the composition.

2. The method of claim 1, wherein the hinoki oil comprises from about 0.05% to about 0.4% by weight of the composition.

3. The method of claim 1, wherein the red clover extract comprises from about 1 ppmw to about 500 ppmw of the composition.

4. The method of claim 1, wherein the peptide comprises from about 0.01 ppmw to about 100 ppmw of the composition.

5. The method of claim 1, wherein the red clover extract comprises an isoflavone.

6. The method of claim 1, wherein the peptide comprises at least one peptide selected from the group consisting of: Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, Acetyl Tetrapetide-2, and Myristoyl Pentapeptide-17.

7. The method of claim 1, wherein the peptide is acetyl tetrapeptide-3.

8. The method of claim 1, wherein the composition further comprise a carrier fluid, wherein the carrier fluid is an alcohol free carrier fluid.

9. The method of claim 1, wherein the peptide comprises acetyl tetrapeptide-3, wherein the hinoki oil comprises from about 0.01% to about 1% by weight of the composition, wherein the red clover extract comprises from about 5 ppmw to about 100 ppmw of the composition, and wherein the acetyl tetrapeptide-3 comprises from about 0.05 ppmw to about 10 ppmw by weight of the composition.

10. The method of claim 5, wherein the isoflavone comprises an O-methylated isoflavone.

11. The method of claim 1, wherein the peptide comprises a tetrapeptide.

12. The method of claim 1, wherein the peptide comprises acetyl tetrapeptide-5.

13. The method of claim 1, wherein the peptide is represented by the formula:

A-X-Gly-His-Lys-Y wherein A comprises a monocarboxylic acid, wherein X represents 1 to 3 Lys residues, and wherein Y represents an —OH or —NH2 group.

14. The method of claim 13, wherein the monocarboxylic acid is represented by the formula: HOOC—R, wherein R comprises a linear or branched C1-C24 aliphatic radical.

15. The method of claim 1, wherein the composition is in the form of at least one of a shampoo, a conditioner, or a foamed liquid.

16. The method of claim 1, wherein the composition further comprises rosemary oil.

17. The method of claim 1, wherein the composition further comprises tea tree oil.

* * * * *